United States Patent
McIntyre et al.

(10) Patent No.: US 11,420,366 B2
(45) Date of Patent: Aug. 23, 2022

(54) METHOD OF MANUFACTURING A STIFF ENGINEERED COMPOSITE

(71) Applicant: Ecovative Design LLC, Green Island, NY (US)

(72) Inventors: Gavin R. McIntyre, Troy, NY (US); Jeffrey D. Betts, Newtoen, PA (US); Gregory Tudryn, New Baltimore, NY (US); Liam Mooney, Olympia, WA (US)

(73) Assignee: Ecovative Design LLC, Green Island, NY (US)

( * ) Notice: Subject to any disclaimer, the term of this patent is extended or adjusted under 35 U.S.C. 154(b) by 186 days.

(21) Appl. No.: 15/258,685

(22) Filed: Sep. 7, 2016

(65) Prior Publication Data

US 2017/0028600 A1 Feb. 2, 2017

Related U.S. Application Data

(62) Division of application No. 14/510,912, filed on Oct. 9, 2014, now abandoned.
(Continued)

(51) Int. Cl.
*C12N 1/14* (2006.01)
*B29C 44/34* (2006.01)
(Continued)

(52) U.S. Cl.
CPC .......... *B29C 44/3415* (2013.01); *B27N 3/002* (2013.01); *B27N 3/18* (2013.01);
(Continued)

(58) Field of Classification Search
CPC ...... C08L 97/02; C08L 15/00–16; C08L 3/02; C08L 89/00; B29C 44/3415; B29C 44/50;
(Continued)

(56) References Cited

U.S. PATENT DOCUMENTS 1,979,176 A 10/1934 Schicht
2,509,984 A 5/1950 Morrow
(Continued)

FOREIGN PATENT DOCUMENTS

CN 1059662 A 3/1992
CN 1732887 A 2/2006
(Continued)

OTHER PUBLICATIONS

Nathan J. Kotlarewski; Benoit Belleville; Benson K. Gusamo; Barbara Ozarska. "Mechanical properties of Papua New Guinea balsa wood". Eur. J. Wood Prod. (2016) 74:83-89 (Year: 2016).*
(Continued)

*Primary Examiner* — Michael M Dollinger
*Assistant Examiner* — Christina H. W. Rosebach
(74) *Attorney, Agent, or Firm* — Knobbe Martens Olson & Bear, LLP

(57) ABSTRACT

The method of making a compressed biocomposite body includes compressing a mass of biocomposite material comprised of discrete particles and a network of interconnected glucan-containing mycelia cells in the presence of heat and moisture into a compressed body having a density in excess of 18 pcf. Compression may take place batch wise in a press or continuously in a path of narrowing cross-section defined by a series of heated rollers.

21 Claims, 1 Drawing Sheet

Related U.S. Application Data

(60) Provisional application No. 61/890,433, filed on Oct. 14, 2013.

(51) Int. Cl.
  B27N 3/00 (2006.01)
  B27N 3/18 (2006.01)
  C08L 89/00 (2006.01)
  C08L 97/02 (2006.01)
  C08L 3/02 (2006.01)
  B29C 44/50 (2006.01)
  *B27N 3/02* (2006.01)
  *B27N 7/00* (2006.01)
  *B27N 3/20* (2006.01)
  *B27N 3/04* (2006.01)
  *B29L 31/44* (2006.01)

(52) U.S. Cl.
  CPC ............... B29C 44/50 (2013.01); C08L 3/02 (2013.01); C08L 89/00 (2013.01); C08L 97/02 (2013.01); C12N 1/14 (2013.01); *B27N 3/02* (2013.01); *B27N 3/04* (2013.01); *B27N 3/20* (2013.01); *B27N 7/005* (2013.01); *B29K 2995/0063* (2013.01); *B29L 2031/44* (2013.01)

(58) Field of Classification Search
  CPC .. C12P 1/02; C12N 1/14; B27N 3/002; B27N 3/18; B27N 3/02; B27N 3/04; B27N 3/20; B27N 3/005; B29K 2995/0063; B29L 2031/44
  See application file for complete search history.

(56) References Cited

U.S. PATENT DOCUMENTS

| | | |
|---|---|---|
| 2,657,647 A | 11/1953 | Rapisarda |
| 2,723,493 A | 11/1955 | Stoller |
| 2,815,621 A | 12/1957 | Carter |
| 2,964,070 A | 12/1960 | Linhardt |
| 3,268,606 A | 8/1966 | Jaeger |
| 3,316,592 A | 5/1967 | Forrest |
| 3,317,375 A | 5/1967 | Molinet et al. |
| 3,421,554 A | 1/1969 | Carter |
| 3,477,558 A | 11/1969 | Fleischauer |
| 3,499,261 A | 3/1970 | Hullhorst et al. |
| 3,708,952 A | 1/1973 | Schulze et al. |
| 3,717,953 A | 2/1973 | Kuhn et al. |
| 3,782,033 A | 1/1974 | Hickerson |
| 3,810,327 A | 5/1974 | Giansante |
| 3,828,470 A | 8/1974 | Stoller |
| 3,961,938 A | 6/1976 | Iizuka et al. |
| 4,027,427 A | 6/1977 | Stoller et al. |
| 4,036,122 A | 7/1977 | Langen |
| 4,038,807 A | 8/1977 | Beardsley et al. |
| 4,063,383 A | 12/1977 | Green |
| 4,073,956 A | 2/1978 | Yates |
| 4,127,965 A | 12/1978 | Mee |
| 4,136,767 A | 1/1979 | Sarovich |
| 4,226,330 A | 10/1980 | Butler |
| 4,263,744 A | 4/1981 | Stoller |
| 4,265,915 A | 5/1981 | MacLennan et al. |
| 4,294,929 A | 10/1981 | Solomons et al. |
| 4,337,594 A | 7/1982 | Hanacek et al. |
| 4,370,159 A | 1/1983 | Holtz |
| 4,568,520 A | 2/1986 | Ackermann et al. |
| 4,620,826 A | 11/1986 | Rubio et al. |
| 4,716,712 A | 1/1988 | Gill |
| 4,722,159 A | 2/1988 | Watanabe et al. |
| 4,878,312 A | 11/1989 | Shimizu |
| 4,922,650 A | 5/1990 | Akao et al. |
| 4,960,413 A | 10/1990 | Sagar et al. |
| 5,021,350 A | 6/1991 | Jung et al. |
| 5,030,425 A | 7/1991 | Bowers-Irons et al. |
| 5,074,959 A | 12/1991 | Yamanaka et al. |
| 5,085,998 A | 2/1992 | Lebron et al. |
| 5,088,860 A | 2/1992 | Stockdale et al. |
| 5,123,203 A | 6/1992 | Hiromoto |
| 5,230,430 A | 7/1993 | Kidder |
| 5,306,550 A | 4/1994 | Nishiyama et al. |
| 5,335,770 A | 8/1994 | Baker et al. |
| 5,370,714 A | 12/1994 | Ogawa |
| 5,433,061 A | 7/1995 | Hutchinson et al. |
| 5,440,860 A | 8/1995 | Meli et al. |
| 5,475,479 A | 12/1995 | Hatakeyama et al. |
| 5,498,384 A | 3/1996 | Volk et al. |
| 5,503,647 A | 4/1996 | Dahlberg et al. |
| 5,511,358 A | 4/1996 | Morita et al. |
| 5,532,217 A | 7/1996 | Silver et al. |
| 5,569,426 A | 10/1996 | Le Blanc |
| 5,589,390 A | 12/1996 | Higuchi et al. |
| 5,590,489 A | 1/1997 | Hattori et al. |
| 5,598,876 A | 2/1997 | Zanini et al. |
| 5,606,836 A | 3/1997 | Insalaco et al. |
| 5,647,180 A | 7/1997 | Billings et al. |
| 5,681,738 A | 10/1997 | Beelman et al. |
| 5,682,929 A | 11/1997 | Maginot et al. |
| 5,685,124 A | 11/1997 | Jandl |
| 5,711,353 A | 1/1998 | Ichikawa et al. |
| 5,802,763 A | 9/1998 | Milstein |
| 5,854,056 A | 12/1998 | Dschida |
| 5,888,803 A | 3/1999 | Starkey |
| 5,897,887 A | 4/1999 | Haeberli |
| 5,919,507 A | 6/1999 | Beelman et al. |
| 5,944,928 A | 8/1999 | Seidner |
| 5,948,674 A | 9/1999 | Mankiewicz |
| 5,979,109 A | 11/1999 | Sartor et al. |
| 6,041,544 A | 3/2000 | Kananen et al. |
| 6,041,835 A | 3/2000 | Price |
| 6,098,677 A | 8/2000 | Wegman et al. |
| 6,112,504 A | 9/2000 | McGregor et al. |
| 6,197,573 B1 | 3/2001 | Suryanarayan et al. |
| 6,226,962 B1 | 5/2001 | Eason et al. |
| 6,300,315 B1 | 10/2001 | Liu |
| 6,306,921 B1 | 10/2001 | Al Ghatta et al. |
| 6,329,185 B1 | 12/2001 | Kofod et al. |
| 6,349,988 B1 | 2/2002 | Foster et al. |
| 6,402,953 B1 | 6/2002 | Gorovoj et al. |
| 6,425,714 B1 | 7/2002 | Waddell |
| 6,444,437 B1 | 9/2002 | Sporleder et al. |
| 6,471,993 B1 | 10/2002 | Shastri et al. |
| 6,475,811 B1 | 11/2002 | Babcock |
| 6,482,942 B1 | 11/2002 | Vittori |
| 6,491,480 B2 | 12/2002 | Waddell |
| 6,500,476 B1 | 12/2002 | Martin et al. |
| 6,523,721 B1 | 2/2003 | Nomoto et al. |
| 6,603,054 B2 | 8/2003 | Chen et al. |
| 6,620,614 B1 | 9/2003 | Lüth et al. |
| 6,660,164 B1 | 12/2003 | Stover |
| 6,679,301 B2 | 1/2004 | Makino et al. |
| 6,726,911 B1 | 4/2004 | Jülich et al. |
| 7,043,874 B2 | 5/2006 | Wasser et al. |
| 7,073,306 B1 | 7/2006 | Hagaman |
| 7,122,176 B2 | 10/2006 | Stamets |
| 7,179,356 B2 | 2/2007 | Aksay et al. |
| 7,395,643 B2 | 7/2008 | Franchini et al. |
| 7,514,248 B2 | 4/2009 | Gower et al. |
| 7,573,031 B2 | 8/2009 | Behar et al. |
| 7,621,300 B2 | 11/2009 | Bonney et al. |
| 7,661,248 B2 | 2/2010 | Conti et al. |
| 7,754,653 B2 | 7/2010 | Hintz |
| 7,836,921 B2 | 11/2010 | Isomura et al. |
| 8,001,719 B2 | 8/2011 | Bayer et al. |
| 8,205,646 B2 | 6/2012 | Isomura et al. |
| 8,227,224 B2 | 7/2012 | Kalisz et al. |
| 8,227,233 B2 | 7/2012 | Kalisz et al. |
| 8,241,415 B2 | 8/2012 | Wantling et al. |
| 8,298,810 B2 | 10/2012 | Rocco et al. |
| 8,313,939 B2 | 11/2012 | Kalisz et al. |
| 8,517,064 B2 | 8/2013 | Isomura et al. |
| 8,658,407 B2 | 2/2014 | Lyons et al. |
| 8,763,653 B2 | 7/2014 | Weigel et al. |
| 8,999,687 B2 | 4/2015 | Bayer et al. |

(56) References Cited

U.S. PATENT DOCUMENTS

| | | | |
|---|---|---|---|
| 9,079,978 B2 | 7/2015 | Räsänen et al. | |
| 9,085,763 B2 | 7/2015 | Winiski et al. | |
| 9,253,889 B2 | 2/2016 | Bayer et al. | |
| 9,332,779 B2 | 5/2016 | Marga | |
| 9,394,512 B2 | 7/2016 | Bayer et al. | |
| 9,469,838 B2 | 10/2016 | Schaak et al. | |
| 9,485,917 B2 | 11/2016 | Bayer et al. | |
| 9,555,395 B2 | 1/2017 | Araldi et al. | |
| 9,714,180 B2 | 7/2017 | McIntyre et al. | |
| 9,752,122 B2 | 9/2017 | Marga et al. | |
| 9,795,088 B2 | 10/2017 | Bayer et al. | |
| 9,801,345 B2 | 10/2017 | Bayer et al. | |
| 9,803,171 B2 | 10/2017 | Bayer et al. | |
| 9,879,219 B2 | 1/2018 | McIntyre et al. | |
| 9,914,906 B2 | 3/2018 | Winiski et al. | |
| 10,125,347 B2 | 11/2018 | Winiski | |
| 10,144,149 B2 | 12/2018 | Araldi et al. | |
| 10,154,627 B2 | 12/2018 | McIntyre et al. | |
| 10,172,301 B2 | 1/2019 | McNamara et al. | |
| 10,266,695 B2 | 4/2019 | Lucht et al. | |
| 10,407,675 B2 | 9/2019 | Bayer et al. | |
| 10,525,662 B2 | 1/2020 | Bayer et al. | |
| 10,537,070 B2 | 1/2020 | Betts et al. | |
| 10,583,626 B2 | 3/2020 | Bayer et al. | |
| 10,589,489 B2 | 3/2020 | Bayer et al. | |
| 10,687,482 B2 | 6/2020 | Ross et al. | |
| 10,785,925 B2 | 9/2020 | McNamara et al. | |
| 11,266,085 B2 | 3/2022 | Kaplan-Bie et al. | |
| 2001/0012235 A1 | 8/2001 | Schuchardt | |
| 2002/0110427 A1 | 8/2002 | Waddell | |
| 2002/0131828 A1 | 9/2002 | Waddell | |
| 2002/0131933 A1 | 9/2002 | Delmotte | |
| 2003/0017565 A1 | 1/2003 | Echigo et al. | |
| 2003/0056451 A1 | 3/2003 | Pisek et al. | |
| 2003/0121201 A1 | 7/2003 | Dahlberg et al. | |
| 2003/0232895 A1 | 12/2003 | Omidian et al. | |
| 2004/0000090 A1 | 1/2004 | Miller | |
| 2004/0020553 A1 | 2/2004 | Amano | |
| 2004/0166576 A1 | 8/2004 | Sadaie | |
| 2004/0177585 A1 | 9/2004 | Vermette | |
| 2005/0133536 A1 | 6/2005 | Kelsey et al. | |
| 2005/0137272 A1 | 6/2005 | Gaserod et al. | |
| 2006/0134265 A1 | 6/2006 | Beukes | |
| 2006/0280753 A1 | 12/2006 | McNeary | |
| 2007/0079944 A1 | 4/2007 | Amidon et al. | |
| 2007/0196509 A1 | 8/2007 | Riman et al. | |
| 2007/0225328 A1 | 9/2007 | Fritz et al. | |
| 2007/0227063 A1 | 10/2007 | Dale et al. | |
| 2007/0294939 A1 | 12/2007 | Spear et al. | |
| 2008/0017272 A1 | 1/2008 | Isomura et al. | |
| 2008/0046277 A1 | 2/2008 | Stamets | |
| 2008/0047966 A1 | 2/2008 | Carson | |
| 2008/0145577 A1 | 6/2008 | Bayer et al. | |
| 2008/0234210 A1 | 9/2008 | Rijn et al. | |
| 2008/0295399 A1 | 12/2008 | Kawai et al. | |
| 2008/0296295 A1 | 12/2008 | Kords et al. | |
| 2009/0107040 A1 | 4/2009 | Vandnhove | |
| 2009/0191289 A1 | 7/2009 | Lutz et al. | |
| 2009/0241623 A1 | 10/2009 | Matano et al. | |
| 2009/0246467 A1 | 10/2009 | Delantar | |
| 2009/0272758 A1 | 11/2009 | Karwacki et al. | |
| 2009/0307969 A1* | 12/2009 | Bayer | A01G 18/64 47/1.1 |
| 2009/0321975 A1 | 12/2009 | Schlummer | |
| 2010/0101190 A1 | 4/2010 | Dillon | |
| 2010/0158976 A1 | 6/2010 | O'Brien et al. | |
| 2010/0159509 A1 | 6/2010 | Xu et al. | |
| 2010/0199601 A1 | 8/2010 | Boldrini et al. | |
| 2010/0227931 A1 | 9/2010 | Kuwano et al. | |
| 2010/0243135 A1 | 9/2010 | Pepper et al. | |
| 2010/0326564 A1 | 12/2010 | Isomura et al. | |
| 2011/0094154 A1 | 4/2011 | Joaquin | |
| 2011/0108158 A1 | 5/2011 | Huwiler et al. | |
| 2011/0265688 A1 | 11/2011 | Kalisz et al. | |
| 2011/0268980 A1 | 11/2011 | Kalisz et al. | |
| 2011/0269209 A1 | 11/2011 | Rocco et al. | |
| 2011/0269214 A1 | 11/2011 | Kalisz et al. | |
| 2011/0306107 A1 | 12/2011 | Kalisz et al. | |
| 2012/0000165 A1 | 1/2012 | Williams | |
| 2012/0006446 A1 | 1/2012 | Isomura et al. | |
| 2012/0060446 A1 | 3/2012 | Merz | |
| 2012/0076895 A1 | 3/2012 | Kirejevas et al. | |
| 2012/0115199 A1 | 5/2012 | Li et al. | |
| 2012/0132314 A1 | 5/2012 | Weigel et al. | |
| 2012/0135504 A1 | 5/2012 | Ross | |
| 2012/0225471 A1 | 9/2012 | McIntyre et al. | |
| 2012/0227899 A1 | 9/2012 | McIntyre et al. | |
| 2012/0231140 A1 | 9/2012 | Hofmann et al. | |
| 2012/0270031 A1 | 10/2012 | Guan et al. | |
| 2012/0270302 A1 | 10/2012 | Bayer et al. | |
| 2012/0315687 A1 | 12/2012 | Bayer et al. | |
| 2013/0095560 A1 | 4/2013 | McIntyre et al. | |
| 2013/0105036 A1 | 5/2013 | Smith et al. | |
| 2013/0210327 A1 | 8/2013 | Corominas | |
| 2013/0224840 A1 | 8/2013 | Bayer et al. | |
| 2013/0274892 A1 | 10/2013 | Lelkes et al. | |
| 2013/0309755 A1 | 11/2013 | McIntyre et al. | |
| 2014/0038619 A1 | 2/2014 | Moulsley | |
| 2014/0056653 A1 | 2/2014 | Scully et al. | |
| 2014/0069004 A1 | 3/2014 | Bayer et al. | |
| 2014/0093618 A1 | 4/2014 | Forgacs et al. | |
| 2014/0163142 A1* | 6/2014 | Zhang | C09J 161/12 524/14 |
| 2014/0173977 A1 | 6/2014 | Juscius | |
| 2014/0371352 A1 | 12/2014 | Dantin et al. | |
| 2015/0033620 A1 | 2/2015 | Greetham et al. | |
| 2015/0038619 A1 | 2/2015 | McIntyre et al. | |
| 2015/0101509 A1 | 4/2015 | McIntyre et al. | |
| 2015/0197358 A1 | 7/2015 | Larsen | |
| 2015/0342138 A1 | 12/2015 | Bayer et al. | |
| 2015/0342224 A1 | 12/2015 | Medoff | |
| 2016/0002589 A1 | 1/2016 | Winiski | |
| 2016/0264926 A1 | 9/2016 | Winiski et al. | |
| 2016/0355779 A1 | 12/2016 | Ross | |
| 2017/0000040 A1 | 1/2017 | Bayer et al. | |
| 2017/0071214 A1 | 3/2017 | Rehage | |
| 2017/0218327 A1 | 8/2017 | Amstislavski et al. | |
| 2017/0253849 A1 | 9/2017 | Miller et al. | |
| 2017/0253852 A1 | 9/2017 | Bayer et al. | |
| 2018/0014468 A1 | 1/2018 | Ross et al. | |
| 2018/0148682 A1* | 5/2018 | Ross | A01G 18/20 |
| 2018/0282529 A1 | 10/2018 | Kaplan-Bie | |
| 2018/0368337 A1 | 12/2018 | McIntyre et al. | |
| 2019/0059431 A1 | 2/2019 | Kozubal et al. | |
| 2019/0090436 A1 | 3/2019 | Betts et al. | |
| 2019/0284307 A1 | 9/2019 | Chase et al. | |
| 2019/0322997 A1 | 10/2019 | Schaak | |
| 2019/0330668 A1 | 10/2019 | Kozubal et al. | |
| 2019/0338240 A1 | 11/2019 | Carlton et al. | |
| 2019/0357454 A1 | 11/2019 | Mueller et al. | |
| 2019/0359931 A1 | 11/2019 | Mueller et al. | |
| 2019/0390156 A1 | 12/2019 | Bayer et al. | |
| 2020/0024577 A1 | 1/2020 | Carlton et al. | |
| 2020/0025672 A1 | 1/2020 | Scullin et al. | |
| 2020/0055274 A1 | 2/2020 | Bayer et al. | |
| 2020/0095535 A1 | 3/2020 | Kozubal et al. | |
| 2020/0102530 A1 | 4/2020 | Winiski et al. | |
| 2020/0146224 A1 | 5/2020 | Kaplan-Bie et al. | |
| 2020/0157506 A1 | 5/2020 | Bayer et al. | |
| 2020/0208097 A1 | 7/2020 | Winiski | |
| 2020/0239830 A1 | 7/2020 | O'Brien et al. | |
| 2020/0268031 A1 | 8/2020 | Macur et al. | |
| 2020/0270559 A1 | 8/2020 | Macur et al. | |
| 2020/0392341 A1 | 12/2020 | Smith et al. | |
| 2021/0127601 A9 | 5/2021 | Kaplan-Bie et al. | |
| 2021/0317433 A9 | 10/2021 | Schaak | |
| 2021/0348117 A9 | 11/2021 | Winiski | |
| 2021/0401019 A1 | 12/2021 | Bayer et al. | |

FOREIGN PATENT DOCUMENTS

| | | |
|---|---|---|
| CN | 101248869 A | 8/2008 |
| CN | 101653081 A | 2/2010 |
| CN | 106947702 A | 7/2017 |

(56) References Cited

FOREIGN PATENT DOCUMENTS

| | | |
|---|---|---|
| EP | 0226292 A1 | 6/1987 |
| EP | 1312547 A1 | 5/2003 |
| EP | 2677030 A1 | 12/2013 |
| EP | 2735318 A1 | 5/2014 |
| EP | 2875805 A1 | 5/2015 |
| EP | 2878340 A1 | 6/2015 |
| EP | 2485779 B1 | 2/2018 |
| EP | 3292769 A1 | 3/2018 |
| GB | 142800 A | 1/1921 |
| GB | 1525484 A | 9/1978 |
| GB | 2032456 A | 5/1980 |
| GB | 2165865 A | 4/1986 |
| IN | 358266 B | 7/2020 |
| JP | H03234889 A | 10/1991 |
| JP | H049316 A | 1/1992 |
| JP | 6111510 B1 | 4/2017 |
| KR | 20050001175 A | 1/2005 |
| KR | 101851655 B1 | 4/2018 |
| WO | WO 1999/024555 | 5/1999 |
| WO | WO 2001/087045 | 11/2001 |
| WO | WO 2005/067977 | 7/2005 |
| WO | WO 2008/025122 | 3/2008 |
| WO | WO 2008/073489 | 6/2008 |
| WO | WO 2010/005476 | 1/2010 |
| WO | WO 2012/122092 | 9/2012 |
| WO | WO 2014/039938 | 3/2014 |
| WO | WO 2014/195641 | 12/2014 |
| WO | WO 2016/149002 | 9/2016 |
| WO | WO 2017/056059 | 4/2017 |
| WO | WO 2017/120342 | 7/2017 |
| WO | WO 2017/136950 | 8/2017 |
| WO | WO 2017/151684 | 9/2017 |
| WO | WO 2017/205750 | 11/2017 |
| WO | WO 2018/011805 | 1/2018 |
| WO | WO 2018/014004 | 1/2018 |
| WO | WO 2018/064968 | 4/2018 |
| WO | WO 2018/183735 | 10/2018 |
| WO | WO 2018/189738 | 10/2018 |
| WO | WO 2019/046480 | 3/2019 |
| WO | WO 2019/099474 | 5/2019 |
| WO | WO 2019/178406 | 9/2019 |
| WO | WO 2019/217175 | 11/2019 |
| WO | WO 2019/226823 | 11/2019 |
| WO | WO 2019/246636 | 12/2019 |
| WO | WO 2020/023450 | 1/2020 |
| WO | WO 2020/072140 | 4/2020 |
| WO | WO 2020/082043 | 4/2020 |
| WO | WO 2020/082044 | 4/2020 |
| WO | WO 2020/102552 | 5/2020 |
| WO | WO 2020/106743 | 5/2020 |
| WO | WO 2020/176758 | 9/2020 |
| WO | WO 2020/186068 | 9/2020 |
| WO | WO 2020/186169 | 9/2020 |
| WO | WO 2020/237201 | 11/2020 |

OTHER PUBLICATIONS

Nathan J. Kotlarewski; Benoit Belleville; Benson K. Gusamo; Barbara Ozarska. Mechanical properties of Papua New Guinea balsa wood.Eur. J. Wood Prod. (2016) 74:83-89. DOI 10.1007/s00107-015-0983-0 (Year: 2016).*

G Newaz; M Mayeed; A Rasul. Characterization of balsa wood mechanical properties required for continuum damage mechanics analysis. J Materials: Design and Applications 2016, vol. 230(1) 206-218. (Year: 2016).*

D. W. Green; J. E. Winandy; D. E. Kretschmann. "Mechanical Properties of Wood". Forest Products Laboratory. 1999. Wood handbook—Wood as an engineering material. Gen. Tech. Rep. FPL-GTR-113. Madison, WI: U.S.D.A. Accessed at https://www.fpl.fs.fed.us/documnts/fplgtr/fplgtr113/ch04.pdf on Jul. 20, 2021. (Year: 1999).* www.timberpress.com/blog/2017/01/how-do-mushrooms-grow-so-quickly/.

Bartnicki-Garcia, "Cell wall chemistry, morphogenesis, and taxonomy of fungi", Annual Review Microbiol. (1968) 22(1): 87-108.

Cha et al., "Biomimetic synthesis of ordered silica structures mediated by block copolypeptides". Nature (2000) 403(6767): 289-292.

Dugdale J. "This new surf company is making boards of mushrooms". Blog post—Jun. 25, 2015.

Halseide P., "Cutting brick the safe way". The Aberdeen Group (1988) Publication #M880354 in 2 pages.

Highland Woodworking, "Making Thin Lumber and Veneer Out of Ordinary Boards", Sales Website (2017) in 3 pages.

Holt et al., "Biobased Composition Boards Made from Cotton Gin and Guayule Wastes: Select Physical and Mechanical Properties", Int J Mater Prod Tech. (2009) 36: 104-114.

Islam et al., "Morphology and mechanics of fungal mycelium", Scientific Reports, (2017) 7(1): 1-12.

Kerem et al., "Chemically defined solid-state fermentation of Pleurotus Ostreatus". Enzyme Microbiol Tech. (1993) 15(9): 785-790.

Kokubo et al., "Ca,P-rich layer formed on high-strength bioactive glass-ceramic A-W". J Biomed Mater Res. (1990) 24(3): 331-343.

Koutsoukos et al., "Precipitation of calcium carbonate in aqueous solutions". J Chem Soc., Faraday Trans. 1, Physical Chemistry in Condensed Phases, (1984) 80(5): 1181-1192.

Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.

Molvinger et al., "Porous chitosan-silica hybrid microspheres as a potential catalyst". Chem Mater. (2004) 16(17): 3367-3372.

Monmaturapoj et al., "Influence of preparation method on hydroxyapatite porous scaffolds". Bull Mater Sci. (2011) 34(7): 1733-1737.

Manoli et al., "Crystallization of calcite on chitin". J Cryst Growth, (1997) 182(1-2): 116-124.

Mushroom Source, "Aspen Wood Shavings for Mushroom Cultivation", Website (2015) in 2 pages.

National Institute of Health (NIH/NIBIB), "Tissue Engineering and Regenerative Medicine", Retrieved Sep. 24, 2018 from https://www.nibib.nih.gov/science-education/science-topics/tissue-engineering-and-regenerative-medicine in 13 pages.

Passauer U. et al., "Pilze in Höhlen" [Cave Mushrooms]. Denisia (2016) 37: 211-224.

Stewart B., "Concrete Fence Posts: Fact Sheet", Texas Agriculture Extension Service, Texas A & M University (1975) Article L-1368 in 4 pages.

Trinci et al., "II. Unrestricted Growth of Fungal Mycelia", The Mycota—Growth, Differenciation and Sexuality by Wessels et al. [Eds], Springer, Berlin, Heidelberg, (1994) Chapter II: 175-193.

Udawatte et al., "Solidification of xonotlite fibers with chitosan by hydrothermal hot pressing". J Mater Sci. Lttrs. (2000) 45(6): 298-301.

University of Sydney, "Competition Between Fungi". Webpage, accessed Jul. 16, 2014—http://bugs.bio.usyd.edu.au/learning/resources/Mycology/Ecology/competition.shtml in 3 pages.

Varma et al., "Porous calcium phosphate coating over phosphorylated chitosan film by a biomimetic method". Biomaterials (1999) 20(9): 879-884.

Wagner A. "Mycelium Biking—Eco-Design at its Best", Master's Thesis at Lulea University of Technology (2016) in 92 pages.

Woller R. "The Pearl Oyster Mushroom", University of Wisconsin Website (2011) in 2 pages.

Wan-Mohtar et al., "The morphology of Ganoderma lucidum mycelium in a repeated-batch fermentation for exopolysaccharide production", Biotechnology Reports (2016) 11:2-11.

Weaver et al., "The stomatopod dactyl club: a formidable damage-tolerant biological hammer". Science (2012) 336(6086): 1275-1280.

Yamasaki et al., "A hydrothermal hot-pressing method: Apparatus and Application". J Mater Sci Lttrs. (1986) 5(3): 355-356.

Zivanovic et al., "Changes in Mushroom Texture and Cell Wall Composition Affected by Thermal Processing". J Food Service (2004) 69: 44-49.

(56) References Cited

OTHER PUBLICATIONS

Agnese et al., "Investigating the Influence of Various Plasticizers on the Properties of Isolated Films of Polyvinyl Acetat". The 37th Annual meeting and Exposition of the Controlled Release Society, Jul. 2010, Portland, OR U.S.A.

Amsellem et al., "Long-term preservation of viable mycelia of two mycoherbicidal organisms". Crop Protection (1999) 18: 643-649.

Angelini et al., "Effect of antimicrobial activity of Melaleuca alternifolia essential oil on antagonistic potential of *Pleurotus* species against Trichoderma harzianum in dual culture." World J Microbiol Biotech. (2008) 24(2): 197-202.

Ashiuchi et al., "Isolation of Bacillus subtilis (chungkookjang), a poly-gamma-glutamate producer with high genetic competence". Appl Microbiol Biotechnol. (2011) 57: 764-769.

Bajaj et al., "Poly (glutamic acid)—An emerging biopolymer of commercial interest". Bioresource Tech. (2011) 102(10): 5551-5561.

Baysal et al., "Cultivation of oyster mushroom on waste paper with some added supplementary materials". Biosource Technology (2003) 89: 95-97.

Begum et al., "Bioconversion and saccharification of some lignocellulosic wastes by Aspergillus oryzae ITCC-4857.01 for fermentable sugar production". Elect J Biotech. (2011) (14)5: 3 in 8 pages.

Binder et al., "Phylogenetic and phylogenomic overview of the Polyporales". Mycologia (Nov.-Dec. 2013) 105(6): 1350-1373.

Blanchette et al., "Fungal mycelial mats used as textile by indigenous people of North America", Mycologia (Feb. 20, 2021) pp. 1-7.

Booth et al., "Potential of a dried mycelium formulation of an indigenous strain of Metarhizium anisopliae against subterranean pests of cranberry." Biocontrol Science and Technology (2000) 10: 659-668.

Bowman et al., "The structure and synthesis of the fungal cell wall". Bioassays (2006) 28(8): 799-808.

Chai et al., "β-Glucan Synthase Gene Overexpression and β-Glucans Overproduction in Pleurotus ostreatus Using Promoter Swapping". PLoS ONE (2013) 8(4): e61693 in 7 pages.

Chaudhary et al., "Understanding rice hull ash as fillers in polymers: a review". Silicon Chemistry (2002) 1:281-289.

Collins English Dictionary, "Mould", retrieved from http://collinsdictionary.com/dictionary/english/mould, downloaded on Jul. 13, 2015.

Dias et al., "Synthesis and characterization of chitosan-polyvinyl alcohol-bioactive glass hybrid membranes". Biomatter (2011) 1(1): 114-119.

Elleuche et. al., "Carbonic anhydrases in fungi". Microbiology (2010) 156: 23-29.

Elsacker et al., "Growing living and multifunctional mycelium composites for large-scale formwork applications using robotic abrasive wire-cutting", Construction Bldg Mater. (2021) 283: 122732 in 16 pages.

Fleet G.H., "Cell walls". in The Yeasts, by Rose et al. [Eds.] 2nd Edition. vol. 4. London: Academic Press. (1991) pp. 199-277.

Frandsen R.J.N., "A guide to binary vectors and strategies for targeted genome modification in fungi using Agrobacterium tumefaciens-mediated transformation". J Microbiol Methods (2011) 87: 247-262.

Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.

Goodell et al., "Fungal Decay of Wood: Soft Rot-Brown Rot-white Rot". In Development of Commercial Wood Preservatives; Schultz et al. [Ed.] ACS Symposium Series; American Chemical Society, Washington, D.C. (2008), Chapter 2, pp. 9-31.

Google Report, Complete colonization substrate mushroom (2 pages) Jan. 30, 2018., 2 pages.

Google Dictionary Definition "Composite", downloaded on Nov. 21, 2018; 1 page.

Gourmet Mushroom, Inc., "What is Mushroom?"—Mushroom Facts Mushroom Information—Educational & Science Projects (2004). Downloaded from www.gmushrooms.com, on Nov. 27, 2017; 5 pages.

Heinzkill et al., "Characterization of laccases and peroxidases from wood-rotting fungi (family Coprinaceae)." Appl Environ Microbiol. (1998) 64: 1601-1606.

Horton et al., "Regulation of Dikaryon-Expressed Genes by FRT1 in the Basidiomycete Schizophyllum commune". Fungal Genet Biol. (1999) 26(1): 33-47.

Hyde et al., "The amazing potential of fungi: 50 ways we can exploit fungi industrially". Fungal Diversity (2019) 97(1): 1-136.

Kamzolkina et al., "Micromorphological features of *Pleurotus pulmonarius* (Fr.) Quel. and P. ostreaturs (Jacq.) P. Kumm. Strains in pure and binary culture with yeasts". Tsitologiia (2006) 48(2): 153-160.

Kerem et al., "Effect of Mananese on Lignin Degradation by Pleurotus ostreatus during Solid-State Fermentation". Applied and Environmental Microbiology (1993) 59(12): 4115-4120.

Kilaru et al., "Investigating dominant selection markers for Coprinopsis cinerea: a carboxin resistance system and re-evaluation of hygromycin and phleomycin resistance vectors". Curr Genet. (2009) 55: 543-550.

Kück et al., "New tools for the genetic manipulation of filamentous fungi". Appl Microbiol Biotechnol. (2010) 86: 51-62.

Kuo, 2005-2006. Glossary of Mycological Terms. Mushroom Expert. Com., pp. 1-13; downloaded from http://www.mushroomexpert.com/glossary.html (May 8, 2015).

Li et al., "Preparation and Characterization of Homogeneous Hydroxyapatite/Chitosan Composite Scaffolds via In-Situ Hydration". J Biomaterials Nanobiotech. (2010) 1: 42-49.

Luo et al., "Coprinus comatus: a basidiomycete fungus forms novel spiny structures and infects nematode." Mycologia (2004) 96(6): 1218-1225.

Mushroom Growers' Handbook 1, "Oyster Mushroom Cultivation". Part II, Chapter 5, (2005) pp. 75-85.

Mushroom Growers' Handbook 2, "Shiitake Bag Cultivation", Part I Shiitake. Published by Mush World (2005) Chapter 4, pp. 73-90 and pp. 105-109.

Norvell L., Fungi Biology. Encyclopedia.(2002); 2 pages.

Novoselova et al., "Cocultivation of Pleurotus ostreatus (Jacq.) P. Kumm, with yeasts". Moscow University Biol Sciences Bulletin (2011) 66(3): 102-105.

Peng et al., "Microbial biodegradation of polyaromatic hydrocarbons". FEMS Microbiol Rev. (2008) 32:927-955.

Perez et al., "Myxococcus xanthus induces actinorhodin overproduction and aerial mycelium formation by Streptomyces coelicolor." Microbial Biotech. (2011) 4(2): 175-183.

Philippoussis et al., "Production of Mushrooms Using Agro-Industrial Residues as Substrates", in Biotechnology for Agro-Industrial Residues, Chapter 9, (2009) pp. 163-187.

Poppe J., Mushroom Growers' Handbook 1, 2004, Part II. Chapter 5, "Substrate", pp. 80-81.

Pompei et al., "The Use of Olive Milling Waste-Water for the Culture of Mushrooms on Perlite". Acta Horticulturae (1994) 361:179-185.

Rai et al., "Production of Edible Fungi", in Fungal Biotechnology in Agricultural, Food, and Environmental Applications, D.K. Arora [Ed.], Marcel Dekker, Inc., (2003), Chapter 21, pp. 383-404.

Royse et al., "Influence of substrate wood-chip particle size on shiitake (*Lentinula edodes*) yield". Bioresource Tehnology (2001) 76(3): 229-233.

Sapak et al., "Effect of endophytic bacteria on growth and suppression of Tganoderma infection in oil palm". Int J Agric Biol. (2008) 10(2): 127-132.

Schirp et al., "Production and characterization of natural fiber-reinforced thermoplastic composites using wheat straw modified with the fungus Pleurotus ostreatus". J Appl. Polym Sci. (2006) 102:5191-5201.

Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.

(56) References Cited

OTHER PUBLICATIONS

Science Daily, May 7, 2007, retrieved from the Internet; http://www.sciencedaily.com/releases/2007/05/070506085628.htm., 3 pages.
Sinotech et al., (2015): retrieved from the Internet http://www.sinotech.com/compressionAndTransferMolding.html., 4 pages.
Slater, M. "Young SoRo Entrepreneur Develops Environmentally Friendly Insulation." The Herald of Randolph. Jun. 21, 2007, pp. 1-2.
Staib et al., "Differential expression of the NRG1 repressor controls species-specific regulation of chlamydospore development in Candida albicans and Candida dubliniensis." Molecular Microbiol. (2005) 55(2): 637-652.
Stamets P., "Mycelium Running". Ten Speed Press (2005); pp. 18, 56, 58, 59, 85, 149, 157, 160 and 291 only.
Sundari et al., "Freeze-drying vegetative mycelium of Laccaria fraterna and its subsequent regeneration". Biotechnology Techniques (1999) 13:491-495.
Tartar et al., "Differential expression of chitin synthase (CHS) and glucan synthase (FKS) genes correlates with the formation of a modified, thinner cell wall in in vivo-produced Beauveria bassiana cells." Mycopathologia (2005) 160(4): 303-314.
Téllez-Jurado et al., "Expression of a heterologous laccase by Aspergillus niger cultured by solid-state and submerged fermentations." Enzyme Microbial Tech. (2006) 38(5): 665-669.
Téllez-Téllez et al., "Growth and laccase production by Pleurotus ostreatus in submerged and solid-state fermentation." Appl Microbiol Biotechnol. (2008) 81(4): 675-679.
Ugalde U., "Autoregulatory Signals in Mycelial Fungi" in The Mycota: A Comprehensive Treatise on Fungi as Experimental Systems for Basic and Applied Research. K. Esser [Ed.] Springer Publisher, 2nd Edition (2006) Chapter 11; pp. 203-213.
Universal Oil Field, "Sawdust", downloaded from universaloilfield.org on Aug. 23, 2018, 4 pages.
Vara et al., "Cloning and expression of a puromycin N-acetyl transferase gene from Streptomyces alboniger in Streptomyces lividans and *Escherichia coli*". Gene (1985) 33(22): 197-206.
Visser et al., "Pseudoxylaria as stowaway of the fungus-growing termite nest: Interaction asymmetry between Pseudoxylaria, Termitomyces and free-living relatives". Fungal Ecology (2011)4(5): 322-332.
Volk (2003) "Tom Volk's Fungus of the Month for Oct. 1998". This month's fungus is Pleurotus ostreatus; the Oyster mushroom, pp. 1-4, downloaded from http://botit.botany.wise.edu/toms_fungi/oct98.html on May 8, 2015.
Wang et al., "Influence of fungal elicitors on biosynthesis of natamycin by Streptomyces natalensis HW-2". Appl Microbiol Biothechnol. (2003) 97: 5527-5534.
Wikipedia, "Wood", downloaded on Nov. 26, 2018, 1 page.
Yang et al., "Medicinal Mushroom Ganoderma lucidum as a Potent Elicitor in Production of t-Resveratrol and t-Peceatannol in Peanut Calluses". J Agric Food Chem. (2010) 58(17): 9518-9522.
Zimin et al., "The MaSuRCA genome assembler". Bioinformatics (2013) 29(21): 2669-2677.
Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.
PhpBB Shopsmith Forums, "Cracks in wide paneling boards", Excerpt from Oct. 28, 2017, downloaded from URL <https://www.shopsmith.com/ss_forum/viewtopic.php?p=214601 >; 2 pages.
Antón et al., "PimM, a PAS Domain Positive Regulator of Pimaricin Biosynthesis in Streptomyces natalensis." Microbiol. (2007) 153: 3174-3183.
Appels et al., "Hydrophobin gene deletion and environmental growth conditions impact mechanical properties of mycelium by affecting the density of the material." Scientific Reports (2018)8(1): 1-7.

Arshad et al., "Tissue engineering approaches to develop cultured meat from cells: a mini review." Cogent Food & Agriculture (2017) 3(1): 1320814 in 11 pages.
Belardinelli et al., "Actions of Adenosine and Isoproterenol on Isolated Mammalian Ventricular Myocytes." Circulation Res. (1983) 53(3): 287-297.
Belay et al., "Preparation and Characterization of Graphene-agar and Graphene Oxide-agar Composites." JOAPS (2017) 134(33): 45085.
Bormann et al., "Characterization of a Novel, Antifungal, Chitin-binding Protein from Streptomyces Tendae Tü901 that Interferes with Growth Polarity." J Bacter. (1999) 181(24): 7421-7429.
Bružauskaite et al., "Scaffolds and Cells for Tissue Regernation: Different Scaffold Pore Sizes—Different Cell Effects." Cytotechnology (2016) 68(3): 355-369.
Byrd, "Clean meat's path to your dinner plate", The Good Food Institute, website accessed Nov. 14, 2018, https://www.gfi.org/clean-meats-path-to-commercialization; 11 pages.
Cerimi et al., "Fungi as source for new bio-based materials: a patent review", Fungal Biol Biotechnol. (2019) 6: 17; 10 pgs.
Chi et al., "Can Co-culturing of Two White-rot Fungi Increase Lignin Degradation and the Production of Lignin-degrading Enzymes?" Inter'l Biodeter Biodegrad. (2007) 59(1): 32-39.
Glowacki et al., "Bioconjugation of Hydrogen-bonded Organic Semiconductors with Functional Proteins." J Mate Chem. C (2015) 3(25): 6554-6564.
Greetham et al., "Pheotypic characterisation of *Saccharomyces sensu* stricto to Inhibitory Compounds Released During the Deconstruction of Lignocellulosic Material." 3th International Congress on Yeasts, ICY 2012, Aug. 26-30, Madison, USA; 1 page.
Griffin et al., "Regulation of macromolecular synthesis, colony development and specific growth rate of Achlya bisexualis during balanced growth". J General Microbiol. (1974) 80(2): 381-388.
Growers Supply. "Horticultural Coarse Perlite—4 Cubic Fee—Growers Supply". URL: https://growerssupply.com; Growers Supply 2012; www.growerssupply.com/farm/supplies/prod1:gs_growing_mediums:pg111049.html; downloaded Dec. 14, 2020 in 3 pages.
Haneef et al., "Advanced Materials from Fungal Mycelium: Fabrication and Tuning of Physical Properties", Scientific Reports 7(1): 1-11; DOI: 10.1038/srep41292, Jan. 24, 2017.
Heisig et al., USGS, "Ground-Water Resources of the Clifton Park Area, Saratoga County, New York", 2002, retrieved from the internet (Oct. 15, 2016): http://ny.water.usgs.gov/pubs/wri/wri014104/wrir01-4104.pdf; 27 pages.
Home Depot "Miracle Gro® Perlite Mix", retrieved from the internet: http://homedepot.com/p/Miracle-Gro-8-pt-Perlite-Mix-74278430/204502291; 2 pages.
Home Depot "Pennington—Fast Acting Gypsum", retrieved from the internet: http://homedepot.com/p/Miracle-Gro-8-pt-Perlite-Mix-74278430/204502291; 2 pages.
Howden et al., "The effects of breathing 5% CO2 on human cardiovascular responses and tolerance to orthostatic stress". Exper. Physiol. (2004) 89(4): 465-471.
Hüttner et al., "Recent advances in the intellectual property landscape of filamentous fungi", Fungal Biol Biotechnol. (2020) 7:16; 17 pgs.
Instructables, How to Grow Oyster Mushroom Spawn (Low Tech), retrieved from the internet Aug. 19, 2018: http://www.instructables.com/id/1-How-to-Grow-Oyster-Mushroom-Spawn-Low-Tech/; 17 pages.
Jones et al., "Leather-like material biofabrication using fungi", Nature Sustainability (2020) https://doi.org/10.1038/s41893-020-00606-1, Sep. 7, 2020.
Kemppainen et al., "Transformation of the Mycorrhizal Fungus Laccaria Bicolor using Agrobacterium tumefaciens." Bioengin Bugs (2011) 2(1): 38-44.
Kim et al., "Current Technologies and Related Issues for Mushroom Transformation." Mycobiology (2015) 43(1): 1-8.
Kües, U., "Life History and Development Processes in the Basidiomycete Coprinus Cinereus." Micro Molecular Biol Rev. (2000) 64(2): 316-353.
Kuhar et al., by Ingredi Potassium Sorbate vs Campden Tablets in Wine Making; Jun. 4, 2018. [online]; Retrieved from the Internet

(56) References Cited

OTHER PUBLICATIONS

<URL: https://ingredi.com/blog/potassium-sorbate-vs-campden-tables-in-wine-making/>; 2 pages.
McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.
Merriam-Webster, "Chamber" dictionary definition; https://www.merriam-webster.com/dictionary accessed Jul. 10, 2017; in 4 Pages.
Merriam-Webster, "pack" Thesaurus definition; https://www.merriam-webster.com/thesaurus; synonyms accessed Aug. 19, 2019; in 10 Pages.
Michielse et al., "Agrobacterium-mediated Transformation of the Filamentous Fungus Aspergillus Awamori." Nature Protocols (2008) 3(10): 1671-1678.
Mitchell et al., [Eds.] "Solid-State Fermentation Bioreactors." Springer Verlag, Berlin/Heidelberg (2006); TOC in 12 Pages.
Moore D., "Fungal Morphogenesis." Cambridge University Press, Cambridge, UK; (1998) TOC in 8 Pages.
Moore D., "Tolerance of Imprecision in Fungal Morphogenesis." In Proceedings of the 4th Meeting on the Genetics and Cellular Biology of Basidiomycetes (Mar. 1998) pp. 13-19.
Naknean et al., "Factors Affecting Retention and Release of Flavor Compounds in Food Carbohydrates." Inter'l Food Res J. (2010) 17(1): 23-34.
Nussinovitch "Polymer Macro-and Micro-Gel Beads: Fundamentals and Applications", DOI 10.1007/978-1-4419-6618_2, Springer Science & Business Media LLC (2010) TOC in 8 Pages.
Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.
Peksen et al., "Favourable Culture Conditions for mycelial growth of Hydnum repandum, a medicinal mushroom." African Journal of Traditional, Complementary and Alternative Medicines (2013) 10(6): 431-434.
Pinterest Fungus Objects: Alaska and Canada; Collection by Deborah Tear Haynes, downloaded from URL <https://www.pinterest.com/deborahtear/fungi-textile-ketchikan-alaska/>; 1 page.
Ross, P., "Pure Culture" 1997-Present; URL: <http://billhoss.phpwebhosting.com/ross/index.php?kind>; downloaded Dec. 14, 2016 in 11 pages.
Schaner et al., "Decellularized Vein as a Potential Scaffold for Vascular Tissue Engineering." J Vascular Surg. (2004) 40(1): 146-153.
Schuurman J., "Unique agar Pearls." YouTube video; Feb. 16, 2012, <https://www.youtube.com/watch?v=8GqTTOHETPQ>; 1 page.
Seamon K.B., "Forskolin: Unique Diterpene Activator of Adenylate Cyclase in Membranes and in Intact Cells." PNAS (1981) 78(6): 3363-3367.
Stanev et al., "Open Cell Metallic Porous Materials Obtained Through Space Holders. Part I: Production Methods, A Review". JMSE (2016) 139(5): 21 pages.
Stephens et al., "Bringing Cultured Meat to Market: Technical, Socio-political, and Regulatory Challenges in Cellular Agriculture." Trends in Food Science & Technology (2018) 78: 155-166.
Wikipedia, "Water gel (plain)", Wikipedia Contributors downloaded Aug. 21, 2017 in 1 Page.
Xiao et al., "A Water-soluble Core Material for Manufacturing Hollow Composite Sections." Comp. Structures (2017) 182: 380-390.
Zadrazil et al., "Influence of CO2 Concentration on the Mycelium Growth of Three *Pleurotus* Species", European J. Appl. Microbiol., vol. 1, pp. 327-335 (1975).
Abbadi et al., "Immunocytochemical identification and localization of lipase in cells of the mycelium of *Penicillium cyclopium* variety", Applied Microbial Cell Physiology (1995) 42: 923-930.
Ando et al., "Cosmetic material for skin whitening—contains mushroom mycelium cultured matter and e.g. ginseng extract, chondroitin sodium sulphate and/or hyaluronic acid", WPI/THOMSON (Jan. 14, 1992), 1992(8): Accession #1992-062018; Abstract of JP4009316A; in 9 pages.
Attias et al., "Biofabrication of Nanocellulose-Mycelium Hybrid Materials", Adv Sustainable Syst. (2020) 5(2): 2000196 in 12 pages; Supporting Information in 7 pages.
Borrás et al., "Trametes versicolor pellets production: Low-cost medium and scale-up", Biochem Eng J. (2008) 42(1): 61-66.
Holt et al. "Fungal mycelium and cotton plant materials in the manufacture of biodegradable molded packaging material: Evaluation study of select blends of cotton byproducts." J Biobased Mater Bioenergy (2012) 6(4): 431-439.
Jiang et al., "Manufacturing of Natural Composites with a Mycelium Binder and Vacuum-infused Vegetable Oil-based Resins", Poster dated May 2014; 1 page.
Jiang et al., "Vacuum Infusion of Mycelium-Bound Biocomposite Preforms with Natural Resins", CAMX ExpoConference Proceedings, Oct. 13-16, 2014, 13 pages.
Jones et al., "Mycelim Composites: A Review of Engineering Characteristics and Growth Kinetics", J Bionanoscience (2017) 11 (4): 241-257.
Jones et al., "Waste-derived Low-cost Mycelium Composite Construction Materials with Improved Fire Safety", FAM (Fire and Materials) (2018) 42(7): 816-825.
Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.
Pathway-27, "Beta-glucan", Aug. 2012, retrieved from http://http://www.pathway27.eu/topstory/beta-glucan/on Oct. 7, 2021 in 2 pages.
Stamets P., "Growing Gourmet and Medicinal Mushrooms", (1993) Chapter 21; p. 363.
Thomas et al., "Growing Orchids in Perlite". In Perlite Plant Guide, The Schundler Company 1951, pp. 1-6, downloaded from http://www.schundler.com/index.html, archived on May 11, 2015.
Vetchinkina et al., "Bioreduction of Gold (III) Ions from Hydrogen Tetrachloaurate . . ." Scientific Practical J Health Life Sciences No. 4, ISSN 22188-2268, (2013) pp. 51-56.
Wösten et al., "How a fungus escapes the water to grow into the air", Current Biology. (1999) 9(2): 85-88.
Zeng Z., "Cosmetic composition for cleaning skin, comprises glossy ganoderma spores and collagens, content of glossy ganoderma spores in composition and content of collagens in composition", WPI/Thomson (Feb. 5, 2006) 7: Accession #2007-057767; Abstract of CN1732887A; in 11 pages.
Ziegler et al., "Evaluation of Physico-mechanical Properties of Mycelium Reinforced Green Biocomposites Made from Cellulosic Fibers", Appl Engin Agricult. (2016) 32(6): 931-938.
Antinori et al., "Advanced mycelium materials as potential self-growing biomedical scaffolds." Scientific reports (2021) 11(1): 1-14.
Hidayat et al., "Characterization of polylactic acid (PLA)/kenaf composite degradation by immobilized mycelia of *Pleurotus ostreatus*". Inter Biodeter Biodegrad. (2012) 71: 50-54.
Jiang et al., "Bioresin Infused then Cured Mycelium-based Sandwich-structure Biocomposites: Resin Transfer Molding (RTM) Process, Flexural Properties, and Simulation." J Cleaner Production (2019) 207: 123-135.
Jones et al., Chitin-chitosan Thin Films from Microbiologically Upcycled Agricultural By-products. In 13th International Conference on the Mechanical Behavious of Materials, Melbourne, Australia (Jun. 2019) p. 66; in 7 pages.
Meyer et al., "Comparison of the Technical Performance of Leather, Artificial Leather, and Trendy Alternatives." Coatings (Feb. 2021) 11(2): 226; 14 pages.
Wösten et al., "Growing Fungi Structures in Space", ACT Research Category/Space Architecture; Noordwijk, The Netherlands (Oct. 15, 2018) in 17 pages.
Collins English Dictionary, "Cavity", Definition; retrieved on Nov. 8, 2021; 1 page.
Merriam-Webster, "desiccated" (Adj.) Definition; downloaded on Nov. 8, 2021; 1 page.

(56) References Cited

OTHER PUBLICATIONS

Wang et al., "Chemical and structural factors influencing enzymatic saccharification of wood from aspen, birch and spruce". Biomass Bioengin. (2018) 109: 125-134.

Bandalan et al., "Inhibitory effect of garlic (*Allium sativum L.*) against bread mold and its influence on the quality of yeast-leavened bread", Int J Food Engineer. (Dec. 2018) 4(4): 256-262.

Kumla et al., "Cultivation of Mushrooms and Their Lignocellulolytic Enzyme Production Through the Utilization of Agro-Industrial Waste". Molecules Jun. 2020;25(12): 2811 in 41 pages.

Voronin et al., "Carbon and Nitrogen Isotope Composition of the Wood of Pinus sylvestris, Betula pendula and Populus tremula". Paleonotal J., Dec. 2020;54(8): 819-824.

Williams, J. "Waste not: Will the furniture of the future be made from leftovers?", Financial Times Jan. 11, 2019 (Mogu—Radical by Nature); in 9 page.

\* cited by examiner

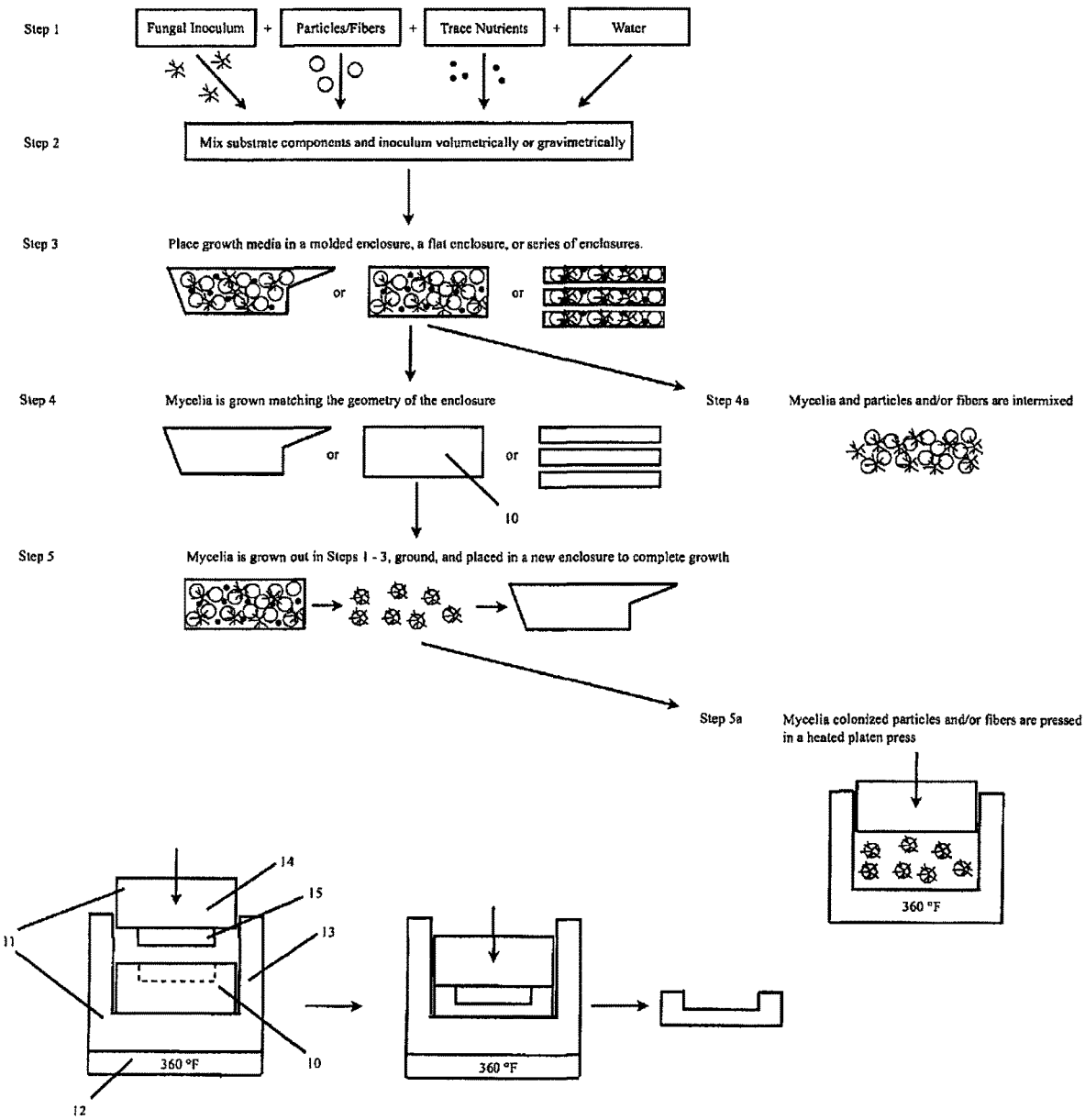

METHOD OF MANUFACTURING A STIFF ENGINEERED COMPOSITE

This application claims the benefit of Provisional Patent Application 61/890,433, filed Oct. 14, 2013 and is a Division of U.S. Ser. No. 14/510,912 filed Oct. 9, 2014.

This invention relates to a method of manufacturing a stiff engineered composite. More particularly, this invention relates to a method of producing stiff mycelium bound parts.

As is known, conventional methods for producing non-structural boards rely on compressing wood veneer sheets, fibers, or particles and binding them together with resin to form composites like hardwood plywood and medium density fiberboard, which are used for applications such as furniture and fixtures, cabinetry, paneling, molding and athletic equipment. The ingredients for these typical non-structural boards require considerable pre-processing, and the feedstocks, especially timber and resins, are subject to considerable price volatility. Additionally, many of the resins used to produce non-structural boards are carcinogenic and can emit volatile organic compounds (VOCs).

Much like nonstructural boards, structural boards are produced by compressing wood veneer sheets, fibers, or particles and binding them together with resin to form composites like oriented strand board (OSB) and softwood plywood. OSB and softwood plywood are used for applications such as wall sheathing, floor sheathing, and concrete framework. These structural boards face the same concerns that nonstructural boards face because they use similar feedstocks and resins.

Many structural and nonstructural boards are used for applications in furniture, cabinetry, and fixtures where they must be cut, milled, and sanded to form the desired shape. Such post processing is expensive and time consuming and creates material waste as the products are shaped. Plastics are also used for these applications and require expensive tools and machines for molding in their production processes.

US Published Patent Application 2008/0145577 describes various techniques for making self-supporting composite bodies comprised of discrete particles and a network of interconnected mycelium cells bonding the particles together. As described therein, the composite bodies may be formed into panels as well as into panel systems with a composite core.

It is an object of this invention to provide an improved process for the manufacture of a compressed composite body of particle/mycelium.

Briefly, the invention provides a method of achieving adhesion between a matrix of fungal mycelium and a slurry of particles and/or fibers (natural or synthetic) through a heated compression process.

US Published Patent Application 2008/0145577 has demonstrated that fungal mycelium can bind natural (lignocellulosic and chitinous waste streams) and/or synthetic (fiberglass) particles together during a controlled incubation process. The mycelium in the latter instance serves as a grown adhesive, digesting a portion of the particles and fibers while encapsulating the slurry in a network of a vegetative tissue.

The process described within demonstrates that the extracellular matrix of mycelium, known as the matrix layer of the cell wall and comprised of polysaccharides (alpha and beta glucans), polymerized amino sugars (N-glucosamine, chitin), monoproteins, and phosopholipids, can serve as a traditional adhesive when heated and dried concurrently. The mycelium is either grown on, or mixed with, an engineered substrate of natural and/or synthetic particles and/or fibers and then compressed under heat and dried to desired geometry.

The heating of the mycelium matrix actually provides value in two places, which makes this process distinctly different from the prior art. The fungal cell wall is comprised of chitin and glucans. The glucans, when heated and saturated with the moisture embedded within the composite, begin to flow like a traditional resin and when dried stick the particles together beyond the traditional mycelium matrix.

By creating sheets of material made from particles bound together with mycelium (hereinafter "the biocomposite material") and compressing these sheets together, bio-based nonstructural boards can be created with feedstocks. The sheets of biocomposite material can be grown together or compressed together with heat to set and dry the final product. The sheets of biocomposite material can vary in product density, fiber content, particle size, and fiber orientation to selectively promote specific mechanical properties (screw hold strength, core shear, modulus of elasticity).

Further, a large mass of mycelium can be cultivated on particles or fibers, milled to a consistent particle size and then pressed in a constrained heated tool.

Additionally, VOCs are not a concern for structural boards produced in this manner because no VOC emitting resins are used in the production process, and the cross-linking occurs between the biochemical construct of the fungal cell wall.

There are significant mechanical advantages garnered from compressing sheets of mycelium bound particles into a single cohesive product with heightened temperatures (200° F.-650° F.) while compressing the biocomposite material at a pressure of from 10 to 1500 psi. These advantages include enhanced modulus of rupture and elasticity (stiffness), and the ability to layer sheets of varying particles size to achieve greater stiffness or dimensional stability (squareness, flatness).

Other materials, including veneers, textiles, or laminates, that are comprised of wood, plastics (polyester scrim), foam, natural fibers, stone, metal, or the like can be grown and bound to the face or internal structure of the mycelium and particle sheets. These laminates can be stacked and interlaid to the mycelium colonized particle sheets, and then compressed to a desired form (flat or molded).

Structural boards can be created by compressing thick blocks of grown material or layered sheets of grown material (particles and/or fibers bound by mycelium) while drying with heat (radiation, conduction, or convective).

Orienting particles within an engineered substrate and then preliminarily binding these with mycelium creates a bio-based product that does not emit VOCs.

The compressed biocomposite material can be easily and cheaply shaped during production. The grown material can be compressed in an inexpensive mold (fiberglass, carbon fiber, composite, wooden and/or metal, e.g. aluminum), giving the material the desired shape and material properties without creating waste. The final product can be dried in the tool to promote cross-linking between the natural polymers within the mycelium, which can occur within the magnitude of minutes.

The grown material can also be compressed in a conductive tool that is heated as well to the final shape, either with a heated platen or inserted cartridges.

These and other objects and advantages of the invention will become more apparent from the following detailed description taken in conjunction with the accompanying drawings wherein:

The FIGURE schematically illustrates the steps in the method of manufacturing a stiff engineered composite in accordance with the invention.

Referring to the FIGURE, in accordance with the method of the invention, an engineered substrate bound with mycelium 10 is grown into a sheet of appropriate dimensions in step 1. In this respect, the basic steps of the method include:

1. Obtain substrate constituents, including fungal inoculum, a bulking collection of particles and/or fibers, a nutrient source or variety of nutrient sources, and water.
2. Combine the substrate constituents by mixing together in volumetric or mass ratios to obtain a solid media with the inoculum (cell and/or tissue culture) added during or following the mixing process.
3. Place the growth media in an enclosure or series of enclosures of the desired geometry.
4. Allow the mycelia to grow through the substrate, creating a composite with a geometry matching the enclosure. This may be either the final geometry or the near net geometry of the final product.

4a. For parts that are dried in compression, the mycelium does not have to grow on the engineered substrate but could be grown in a secondary process and thoroughly intermixed to distribute culture just prior to compressive drying (conduction, convection, radiation).
5. Repeat steps 1-3 for applications where materials are layered or embedded to create the desired final composite media. Alternatively to steps 3 and 4, the growth media may be grown as a solid mass, and then ground up for later steps or placed in an enclosure of the desired shape and then be allowed to regrow into that shape.

In step 2 of the method, the engineered substrate 10 containing some residual moisture and, for example in the form of a flat rectangular plate or tile, is placed in a compression fixture 11, for example, a pinch press 11. As illustrated, the pinch press 11 has a bottom platen 12 that can be heated and that is formed with a mold body 13 of predetermined shape, for example, of semi-cylindrical shape. The pinch press 11 also has a top platen 14 for engaging on the bottom platen 12 with a cavity 15 within the platen 14 for mating about the mold body 13. Typically, when the platens 12, 14 are closed together, a semi-cylindrical gap exists between the mold body 13 and the cavity 15.

Typically, the engineered substrate 10 should contain a minimum of 10% moisture by weight. Steam may also be injected into a dry mass during compression to induce the adhesion.

Since the glucans are activated by steam, the engineered substrate 10 should contain a minimum of 40% moisture by weight so that the moisture may be transformed into steam during the heated pressing process as otherwise live steam would be injected into the dry mass during compression to induce the adhesion.

After positioning of the engineered substrate 10 on the mold body 13 of the pinch press 11, the top platen 14 is lowered onto the bottom platen 12 in order to compress, trim and dry the biocomposite material of the substrate 10.

During operation, the pinch press 11 is heated to 300° F. while compressing the biocomposite material of the substrate to between 10 psi and 1500 psi. The length of time that the biocomposite material of the substrate 10 is retained within the pinch press 11 under heat and pressure is sufficient to the reduce the moisture content of the material to less than 10% by weight and to promote cross-linking between the natural polymers within the mycelium. The biocomposite material can also be held in the pinch press 11 for a time sufficient to achieve a product stiffness that is sufficient to remove the compressed material from the pinch press 11 ("tool" or "buck").

In step 3 of the method, with the pinch press 11 opened, a compressed monolithic body 16 is removed from the pinch press 11. As illustrated, the monolithic body 16 has a semi-cylindrical shape and is characterized as being a rigid shell.

Variations

Additional methods can also be used to produce desirable properties in the final composite.

1. The substrate of engineered particles and/or fibers ("biocomposite material"), either colonized with mycelium (bioactive) or intermixed with mycelium (inactive), can also include cation salts (divalent Na2+ and the like) that can assist with cross-linking between the polysaccharides and amino sugars. Acids (hydrochloric, acetic, lactic) can be provided as well to ensure the substrate stays protonated.

a. The cation salts can be applied during initial substrate preparation and sterilization.

b. The cations can be applied in a solution by either vacuum infusing the solution into the substrate or immersing the substrate in a cation solution for a certain period of time.
2. Surface treatments, such as laminates, veneers, or supplemental fibers, can be bound to the engineered substrate. For example, a laminate can be placed on the face of the engineered substrate during the initial growth step. This is "colonization". Alternatively, a laminate may be applied to the engineered substrate just before pressing and bound with only the glucans.

The laminate treatments are applied to the surfaces, or in between tiles if multiple colonized blocks are used, and pressed with a heated platen until the biocomposite material is <10% moisture.

Laminations and inserts can also be pressed into the surface of a colonized engineered substrate, again using the adhesion from the glucans. The laminations can include non-woven textiles, woven products (jute, fiberglass), and Kraft paper, which become an integrated component of the final part.

Inserts can be positioned in either the lower or upper platens of the compression tooling, and can be pressed into the biological composite during the setting process.

3. The biocomposite material can also be dried to a particular moisture content with conduction, convection, and/or radiation at atmospheric pressure, and then compression dried to complete the process.
4. The biocomposite material can be dried to a moisture content of between 6% and 30% during the heated compression stage to retain enough moisture to impart electrical conductivity such that the resultant compressed monolithic body can be powder coated since a powder coating process requires the material to be electrically conductive and moisture, rather than metals salts, is used to impart this characteristic.

a. The heated compression tool, which forms the final product geometry, can include surface finishes that translate to the final part.
5. The colonized biocomposite material can be compressed and dried with a series of heated rollers that narrow in cross-section as the material is conveyed through the process.

Sheets of biocomposite material can be grown together or compressed together with heat to set and dry the final product. The sheets of biocomposite material can vary in product density, fiber content, particle size, and fiber orientation to selectively promote specific mechanical properties (screw hold strength, core shear, modulus of elasticity). Additionally, VOCs are not a concern for structural boards produced in this manner because no VOC emitting resins are used in the production process, and the cross-linking occurs between the biochemical construct of the fungal cell wall.

There are significant mechanical advantages garnered from compressing sheets of mycelium bound particles into a single cohesive product with heightened temperatures (200° F.-650° F.). These advantages include enhanced modulus of rupture and elasticity (stiffness), and the ability to layer sheets of varying particles size to achieve greater stiffness or dimensional stability (squareness, flatness). Other materials, including veneers, textiles, or laminates, that are comprised of wood, plastics (polyester scrim), foam, natural fibers, stone, metal, or the like can be grown and bound to the face or internal structure of the mycelium and particle sheets. These laminates can be stacked and interlaid to the mycelium colonized particle sheets, and then compressed to a desired form (flat or molded).

The method of the invention allows a final part to have a density between 18 and 60 lbs/ft$^3$, an elastic modulus up to 250 ksi and a modulus of rupture as high as 2500 psi.

Further Variations

Where the growth media is grown as a solid mass and then ground up to produce particles or pellets with mycelium therein, the particles may be poured into an enclosure of the desired shape and then heated and pressed with the process parameters described above. In this embodiment, the final product has a Modulus of Elasticity of 111 psi and a Modulus of Rupture of 2840 psi.

The method provides for crosslinking to occur between the glucans in the mycelia that are solubilized during the compression and moisture release process. This can be further mediated with mild acids that assist in protonating and cross-linking.

EXAMPLE 1

1. Kenaf pith (screened over a 0.375" screen, 42% of mass), maltodextrin (1.6% of mass), calcium sulfate (0.4% of mass), and water (56% of mass) are mixed in an autoclavable bag to form the substrate for fungal growth. For five liters of substrate, the amount of Kenaf pith is 670 grams (g).
2. The bag is sterilized in a pressure cooker at 15 psi and 240° F. for 60 minutes.
3. Millet grain spawn containing fungal tissue is mixed into the substrate (10% [m:m].
4. Plastic tool molds that are 6 inches long, 6 inches wide, and 1 inch deep are filled with inoculated substrate.
5. The substrate is allowed to colonize in the tools for 7 days at ambient laboratory conditions (75° F., 20% relative humidity, 2000 ppm $CO_2$)
6. Wooden veneers that are 6 inches wide by 6 inches long and a square of porous plastic with same dimensions are soaked in 10% hydrogen peroxide for 30 minutes. This is a chemical disinfection method that also imparts the correct amount of water, since hydrogen peroxide oxidizes to water.
7. The substrates in the form of tiles are ejected from the mold and stacked in groups of three with a wooden veneer at each surface and interface and the porous plastic square on the side that will be next to an air inlet during compression.
8. The stack of tiles, veneers, and porous plastic is compressed to approximately 3 times density in a compression frame with an air inlet for forced aeration on one side and holes for passive ventilation on the other. For example, as described in Provisional Patent Application 61/860,386, filed Jul. 31, 2103, the disclosure of which is incorporated herein.
9. The compression frame is hooked up to an air pump and the compressed substrate is subjected to forced aeration for 5 days. Alternatively, the compressed substrate may be dried within the compression frame with convective or conductive drying.
10. The compressed composite body is ejected from the compression frame and placed in an aluminum collar of the same exterior dimensions that surrounds the periphery of the compressed composite body. This collar that has the desired features, locks and creates the features and dimensions required of the final part.
11. A heated platen press (at a force of 20 ton and 600° F.) is compressed onto the pre-compressed body for two minutes, such that the body is dried to <10% moisture content. The resulting part has a density of 20 lbs/ft$^3$, a modulus of elasticity around 80 ksi, a modulus of rupture around 800 psi, and a screw hold strength around 100 lbf.

In this example, the biocomposite material is subjected to compression alone to form a compressed monolithic body, e.g. as described in as described in Provisional Patent Application 61/860,386, filed Jul. 31, 2103, and then subjected to heat and pressure to promote cross-linking between the natural polymers within the mycelium.

EXAMPLE 2

1. Kenaf pith (screened over a 0.375" screen, 42% of mass), maltodextrin (1.6% of mass), calcium sulfate (0.4% of mass), and water (56% of mass) are mixed in an autoclavable bag to form the substrate for fungal growth.
2. The bag is sterilized in a pressure cooker at 15 psi and 240° F. for 60 minutes.
3. Millet grain spawn containing fungal tissue is mixed into the substrate (10% [m:m].
4. Plastic tool molds that are 6 inches long, 6 inches wide, and 1 inch deep are filled with inoculated substrate.
5. The substrate is allowed to colonize in the tools (molds) for 7 days at ambient laboratory conditions (75° F., 20% relative humidity, 2000 ppm $CO_2$)
6. The colonized substrate is ejected from the plastic tool that granted the growing mass its original structure and placed in an aluminum collar that is perforated to allow for water to escape.

The colonized substrate is placed in a heated platen press (20 ton, 600° F.) and is compressed for four minutes, such that the part is dried to <10% moisture content. The colonized substrate requires between 25 psi and 5000 psi to achieve the maximum compression required.

The resulting part has a density of 34 lbs/ft$^3$, a modulus of elasticity around 132 ksi, a modulus of rupture around 1698 psi, and a screw hold strength around 24 lbf at half an inch thickness. By way of comparison, a composite for packaging made in accordance with the methods described in US Published Patent Application 2008/0145577 has a density of from 5 to 8 lbs/ft$^3$.

EXAMPLE 3

1. Kenaf pith (screened over a 0.375" screen, 42% of mass), maltodextrin (1.6% of mass), calcium sulfate (0.4% of mass), and water (56% of mass) are mixed in an autoclavable bag to form the substrate for fungal growth.

2. The bag is sterilized in a pressure cooker at 15 psi and 240° F. for 60 minutes.

3. Millet grain spawn containing fungal tissue is mixed into the substrate (10%) [m:m].

4. Growth enclosure molds that are fabricated out of thermoformed polyethylene plastic to the final product geometry or near net shape are filled with inoculated substrate.

5. The substrate is allowed to colonize in the tools (molds) for 7 days at ambient laboratory conditions (75° F., 20% relative humidity, 2000 ppm $CO_2$)

6. The colonized substrate is ejected from the plastic tool that granted the growing mass its original structure and placed in a structural enclosure of the final product configuration. This second enclosure permits conductive heating and is designed to allow for the installation of embedded inserts or secondary components. The tool is perforated to allow for water to escape.

7. The colonized substrate in the second enclosure is placed in a heated platen press (20 ton, 600° F.) and is compressed for four minutes, such that the part is dried to <10% moisture content.

The resulting part has a density of 29 lbs/ft$^3$, a modulus of elasticity around 120 ksi, a modulus of rupture around 819 psi, and a screw hold strength around 132 lbf at an inch thickness.

EXAMPLE 4

1. Kenaf pith (screened over a 0.375" screen, 42% of mass), maltodextrin (1.6% of mass), calcium sulfate (0.4% of mass), and water (56% of mass) are mixed in an autoclavable bag to form the substrate for fungal growth.

2. The bag is sterilized in a pressure cooker at 15 psi and 240° F. for 60 minutes.

3. Millet grain spawn containing fungal tissue is mixed into the substrate (10%) [m:m].

4. Plastic tool molds that are 18 inches long, 18 inches wide, and 1 inch deep are filled with inoculated substrate.

5. The substrate is allowed to colonize in the tools (molds) for 7 days at ambient laboratory conditions (75° F., 20% relative humidity, 2000 ppm $CO_2$)

6. The colonized substrate, in the form of a sheet, is ejected from the plastic tool and aligned in a heated pinch press of a desired geometry.

7. The colonized part is pressed and heated (300° F.) for one minute, such that the part is dried to <10% moisture content, molded to the desired shape, and excess material trimmed from the final product.

EXAMPLE 5

1. Fabricate the biocomposite material into a flat blank board of 1.25" thickness with a 0.25" hemp nonwoven matt grown into either face.

2. Press the flat blank board into the predetermined curved shape, such as a shape for a chair back, along with surface features under a compressive force of 3000 psi and 340° F. for 10 minutes to lock the surface features and get the board to below 10% moisture.

The surface feature may be obtained by embossing at least one face of the board with a predetermined sculptured feature using an embossing surface on the face of the press that is pressed against the board.

When using a mold (tool), a mold release, such as a spray release or a parchment paper, may be used on the surfaces of the mold to enable an easy ejection of the colonized substrate from the mold.

The invention thus provides a compressed composite body of particle/mycelium that is characterized in being a rigid body having a density in the range of from 18 to 60 lbs/ft$^3$, a modulus of elasticity of up to 250 ksi (1 k=1000 psi) and a modulus of rupture of up to 2500 psi.

The compressed composite body made in accordance with the methods described herein differs from a compressed composite body made in accordance with the methods described in Provisional Patent Application 61/860,386, filed Jul. 31, 2013, inter alia, in that due to conductive drying, the glucans are cross-linked and all the water is removed.

The composite body made in accordance with the invention may be subjected to further processing steps to achieve a desired final product. For example, the composite body may be die cut to a desired three-dimensional shape; drilled or cut to provide openings therein; and the like.

Further, an assemblage of flat sheets of biocomposite material, sheets of woven or non-woven laminations and inserts of three-dimensional contour (i.e. inserts on non-flattened shape) may be heated and pressed together to form a desired final product having an internal shape corresponding to the inserts.

What is claimed is:

1. A self-supporting composite body comprising a substrate of discrete fibers and a network of interconnected mycelia cells extending through and around the discrete fibers and bonding the discrete fibers together, said self-supporting composite body being characterized in being stiff and in having a density between 18 and 60 pounds per cubic foot, a modulus of elasticity greater than 250 ksi and a modulus of rupture of up to 2500 psi.

2. The self-supporting composite body of claim 1, characterized in being of a predetermined shape.

3. The self-supporting composite body of claim 2, said predetermined shape is a deformed geometric shape.

4. The self-supporting composite body of claim 2, wherein said predetermined shape is a curved shape.

5. The self-supporting composite body of claim 2, wherein said predetermined shape is a semi-cylindrical shape.

6. The self-supporting composite body of claim 1, characterized in being a structural board.

7. The self-supporting composite body of claim 1, characterized in being a non-structural board.

8. The self-supporting composite body of claim 1, characterized in being embossed.

9. The self-supporting composite body of claim 1, wherein said self-supporting composite body comprises a predetermined sculptured feature.

10. The self-supporting composite body of claim 1, further comprising at least one layer selected from a group consisting of wood, plastic, foam, natural fibers, stone, metal, non-woven textiles, jute, fiberglass, and Kraft paper.

11. The self-supporting composite body of claim 1, wherein the discrete fibers are selected from a group consisting of lignocellulose, chitin, and fiberglass.

12. The self-supporting composite body of claim 2, further comprising at least one layer selected from a group consisting of wood, plastic, foam, natural fibers, stone, metal, non-woven textiles, jute, fiberglass, and Kraft paper.

13. The self-supporting composite body of claim 2, wherein the discrete fibers are selected from a group consisting of lignocellulose, chitin, and fiberglass.

14. The self-supporting composite body of claim 6, further comprising at least one layer selected from a group consisting of wood, plastic, foam, natural fibers, stone, metal, non-woven textiles, jute, fiberglass, and Kraft paper.

15. The self-supporting composite body of claim 6, wherein the discrete fibers are selected from a group consisting of lignocellulose, chitin, and fiberglass.

16. The self-supporting composite body of claim 7, further comprising at least one layer selected from a group consisting of wood, plastic, foam, natural fibers, stone, metal, non-woven textiles, jute, fiberglass, and Kraft paper.

17. The self-supporting composite body of claim 7, wherein the discrete fibers are selected from a group consisting of lignocellulose, chitin, and fiberglass.

18. The self-supporting composite body of claim 8, further comprising at least one layer selected from a group consisting of wood, plastic, foam, natural fibers, stone, metal, non-woven textiles, jute, fiberglass, and Kraft paper.

19. The self-supporting composite body of claim 8, wherein the discrete fibers are selected from a group consisting of lignocellulose, chitin, and fiberglass.

20. The self-supporting composite body of claim 9, further comprising at least one layer selected from a group consisting of wood, plastic, foam, natural fibers, stone, metal, non-woven textiles, jute, fiberglass, and Kraft paper.

21. The self-supporting composite body of claim 9, wherein the discrete fibers are selected from a group consisting of lignocellulose, chitin, and fiberglass.

* * * * *